(12) United States Patent
Lee et al.

(10) Patent No.: US 7,955,801 B2
(45) Date of Patent: Jun. 7, 2011

(54) METHOD AND APPARATUS FOR DISRUPTING CELLS AND PURIFYING NUCLEIC ACID USING A SINGLE CHIP

(75) Inventors: In-ho Lee, Yongin-si (KR); Jun-hong Min, Yongin-si (KR); Young-rok Kim, Yongin-si (KR); Jae-ho You, Yongin-si (KR); Chang-eun Yoo, Yongin-si (KR); Jeong-gun Lee, Yongin-si (KR); Ki-woong Han, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 124 days.

(21) Appl. No.: 11/639,794

(22) Filed: Dec. 15, 2006

(65) Prior Publication Data

US 2007/0238114 A1   Oct. 11, 2007

(30) Foreign Application Priority Data

Apr. 5, 2006   (KR) .................. 10-2006-0030990

(51) Int. Cl.
*C12Q 1/68* (2006.01)
*C12P 19/34* (2006.01)

(52) U.S. Cl. .......................................... 435/6; 435/91.2

(58) Field of Classification Search ........................ None
See application file for complete search history.

(56) References Cited

U.S. PATENT DOCUMENTS

| 5,234,809 | A | 8/1993 | Boom et al. ............... 435/91 |
| 6,291,166 | B1 | 9/2001 | Gerdes et al. .............. 435/6 |
| 6,936,414 | B2 | 8/2005 | Gundling ................. 435/6 |
| 2003/0096429 | A1 | 5/2003 | Baeumner et al. | |

FOREIGN PATENT DOCUMENTS

| EP | 1650297 A2 | 4/2006 |
| WO | WO 9218514 A1 * | 10/1992 |
| WO | 0146404 A1 | 6/2001 |

OTHER PUBLICATIONS

Li et al. Bacterial adhesion to glass and metal-oxide surfaces. Colloids and Surfaces B: Biointerfaces 36: 81-90 (2004).*
Hofmann, O., et al.; "Laser included disruption of bacterial spores on a microchip"; Lab on a Chip; vol. 5; pp. 374-377; 2005.
Lee, J., et al.; "Microchip-based one step DNA extraction and real-time PCR in one chamber for rapid pathogen identification"; Lab on a Chip; vol. 6; pp. 886-895; 2006.
Liu, R., et al.; "Self-Contained, Fully Integrated Biochip for Sample Preparation, Polymerase Chain Reaction Amplification, and DNA Microarray Detection"; Anal. Chem.; vol. 76; 1824-1831; 2004.
European Search and Examination Report, dated Feb. 13, 2007, for Application No. 06124822.5.
Rudi, K., et al.; "Rapid, Universal Method to Isolate PCR-Ready DNA Using Magnetic Beads"; BioTechniques; vol. 22; pp. 506-511; Mar. 1997.
Deggerdal A., et al.;"Rapid Isolation of PCR-Ready DNA from Blood, Bone Marrow and Cultured Cells, Based on Paramagnetic Beads"; BioTechniques; vol. 22; pp. 554-557; Mar. 1997.

* cited by examiner

*Primary Examiner* — Kenneth R. Horlick
*Assistant Examiner* — Angela M Bertagna
(74) *Attorney, Agent, or Firm* — Cantor Colburn LLP

(57) ABSTRACT

Provided herein is a method and apparatus for disrupting cells and purifying nucleic acids in a single chip. The method comprises irradiating a chip with a laser beam, wherein the chip comprises a solid support on which a cell lysis enhancing metal oxide layer, and a cell binding metal oxide layer have been deposited.

12 Claims, 5 Drawing Sheets

(1 of 5 Drawing Sheet(s) Filed in Color)

METHOD AND APPARATUS FOR DISRUPTING CELLS AND PURIFYING NUCLEIC ACID USING A SINGLE CHIP

This application claims priority to Korean Patent Application No. 10-2006-0030990, filed on Apr. 5, 2006, in the Korean Intellectual Property Office, and all the benefits accruing therefrom under 35 U.S.C. §119, the disclosure of which is incorporated herein in its entirety by reference.

BACKGROUND

1. Field of the Invention

The present invention relates to a method for disrupting cells and purifying nucleic acid. The present invention further relates to an apparatus for disrupting cells and purifying nucleic acids.

2. Description of the Related Art

Methods of isolating DNA from cells are performed using materials that have a tendency for binding to DNA. For example, materials used for DNA isolation include silica, glass fiber, anion exchange resin and magnetic beads (Rudi, K. et al., *Biotechniques* 22, 506-511 (1997); and Deggerdal, A. et al., *Biotechniques* 22, 554-557 (1997)). Furthermore, for the purpose of avoiding manual operation and eliminating operator error, several automatic machines have been developed for high-throughput DNA extraction.

The production of high purity double-stranded plasmid DNA, single-stranded phage DNA, chromosomal DNA, and agarose gel-purified DNA fragments is very important in molecular biology. Ideal methods of purifying DNA should be simple and quick, and include minimal manipulation of samples. The DNA molecules obtained using such methods are ready for direct transformation, restriction enzyme analysis, ligation or sequencing. Such methods are very attractive in the automated production of DNA samples. Automated production of DNA samples is often favored in research and diagnosis labs because such methods avoid manual operation and minimize operator error.

Conventionally, methods of purifying nucleic acids using a solid phase are known. For example, U.S. Pat. No. 5,234,809 discloses a method of purifying nucleic acids using a solid phase, e.g., silica particles, to which nucleic acids are bound. The method of U.S. Pat. No. 5,234,809 includes mixing a starting material, a chaotropic material, and a nucleic acid binding solid phase; separating the solid phase with the nucleic acid bound thereto from the liquid, and washing the solid phase nucleic acid complexes. One disadvantage of this method is that the method is time consuming and complicated, and therefore not suitable for a Lab-On-a-Chip (LOC). Furthermore, another disadvantage of the method is that a chaotropic material is used.

U.S. Pat. No. 6,291,166 discloses a method of archiving nucleic acids using a solid phase matrix. This method is advantageous in that nucleic acids are irreversibly bound to the solid phase matrix. By providing nucleic acids irreversibly bound to the solid phase matrix, it is possible to delay analysis of, or to perform repeated analysis of the nucleic acid solid phase matrix complexes after storage. One disadvantage with this method is that alumina ($Al_2O_3$), which has a positively-charged surface, needs to be rendered hydrophilic which requires the use of basic materials, such as NaOH. Another disadvantage with this method is that the nucleic acids are irreversibly bound to the hydrophilic alumina, and thus cannot be separated from the alumina.

U.S. Pat. No. 6,936,414 discloses a method of separating nucleic acid from a test sample. The method comprises contacting a test sample with a metal oxide support material and a binding buffer to form nucleic acid/metal oxide support material complexes; separating the complexes from the test sample; and eluting the nucleic acid from the metal oxide support material. Although the invention disclosed in U.S. Pat. No. 6,936,414 is similar to the present invention in that binding of metal oxide and nucleic acid is used, the invention disclosed in U.S. Pat. No. 6,936,414 differs from the present invention in that the invention disclosed in U.S. Pat. No. 6,936,414 uses a chaotropic salt and a detergent as binding materials when nucleic acids are bound to the metal oxide support. Advantageously, the present invention does not utilize chaotropic salts or detergents.

In an attempt to determine whether a Lab-On-a-Chip integration of cell lysis and nucleic acid purification could be achieved, the inventors studied methods of disrupting cells and purifying nucleic acid based on the conventional techniques described above. The inventors confirmed that a Lab-On-a-Chip integration could be achieved and developed a technique for performing cell enrichment, cell lysis, and a process of purifying nucleic acids in a single chamber.

BRIEF SUMMARY OF THE INVENTION

In one embodiment, the invention is directed to a method of disrupting cells on a chip. The method comprises irradiating a chip with a laser beam, wherein the chip comprises a solid support comprising a cell lysis enhancing metal oxide layer and a cell binding metal oxide layer.

In another embodiment, the invention is directed to a method of disrupting cells and purifying nucleic acids using a single chip. The method comprises introducing a cell-containing sample solution to a solid support, wherein the solid support comprises a cell lysis enhancing metal oxide layer and a cell binding metal oxide layer, wherein the cells bind with the cell binding metal oxide; irradiating the solid support with a laser to disrupt the cells bound to the cell binding metal oxide to release a nucleic acid that binds with the cell binding metal oxide; introducing a washing buffer to the solid support to wash the cell-containing sample solution that is not bound to the cell binding metal oxide; and introducing a nucleic acid eluting buffer to the solid support to elute the nucleic acid bound to the cell binding metal oxide.

In another embodiment, the invention is directed to a chip comprising a solid support wherein a cell lysis enhancing metal oxide and a cell binding metal oxide are deposited on the solid support.

A method of manufacturing the chip is also provided. The method comprises depositing a cell lysis enhancing metal oxide on a solid support; and depositing a cell binding metal oxide on the solid support.

In another embodiment, the invention is directed to an apparatus for disrupting cells and purifying nucleic acids using a single chip. The apparatus comprises: a chip comprising a solid support, wherein a cell lysis enhancing metal oxide and a cell binding metal oxide are deposited on the solid support; and a laser source for generating a laser.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
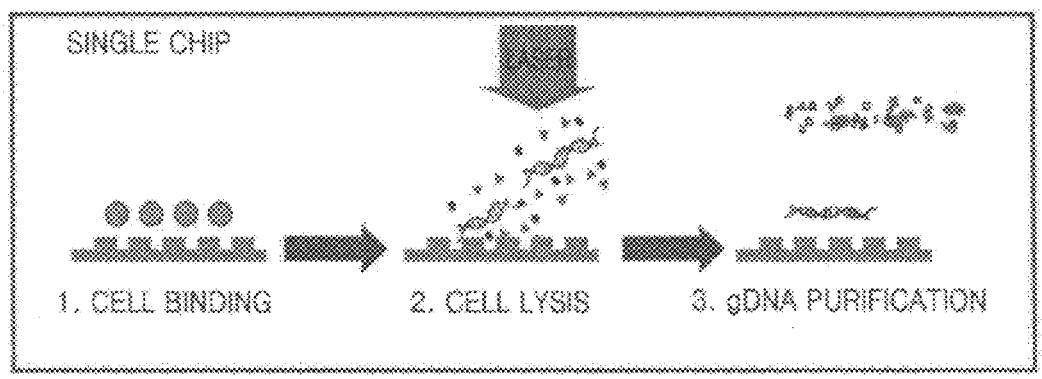
FIG. 1 is a diagram illustrating a method of concentrating cells and purifying nucleic acids from the cells in a single chip or chamber, according to the present invention.

The invention will now be described more fully hereinafter with reference to the accompanying drawings, in which embodiments of the invention are shown. The invention may, however, be embodied in many different forms and should not be construed as limited to embodiments set forth herein. Rather these embodiments are provided so that this disclosure will be thorough and complete, and will fully convey the scope of the invention to those skilled in the art.

In one embodiment, the invention provides a method of disrupting cells on a single chip. The method comprises irradiating a chip with a laser beam, wherein the chip comprises a solid support comprising a cell lysis enhancing metal oxide layer and a cell binding metal oxide layer. In one embodiment, the cell lysis enhancing metal oxide and the cell binding metal oxide layers are sequentially deposited on the solid support.

As used herein the term "cell" means a prokaryotic or eukaryotic cell, a plant cell, a bacterial cell, a pathogenic cell, a yeast cell, an aggregate of cells, a virus, or other nucleic acid-containing biological material, such as, for example, an organelle.

As used herein, the term "nucleic acid" means DNA or RNA. The DNA or RNA can be in any possible configuration, i.e. in the form of double-stranded (DS) nucleic acid, or in the form of single-stranded (ss) nucleic acid, or as a combination thereof (in part ds or ss).

As used herein, the term "cell binding" means the ability to bind a cell or other biomaterial, such as, for example a nucleic acid.

In another advantageous embodiment of the invention, cell disruption and nucleic acid purification are processed in a single chip. For example, a cell lysis enhancing metal oxide is first deposited on a solid support, and then a metal oxide that can bind with cells and nucleic acids is deposited on the solid support, the laser irradiates the solid support to lyse the cells, and then nucleic acids can be purified from the lysed cells in a single chip.

In another embodiment, the invention provides a method of disrupting cells and purifying nucleic acids. The method comprises introducing a cell-containing sample solution to a solid support, wherein the solid support comprises a cell lysis enhancing metal oxide layer and a cell binding metal oxide layer, wherein the cells bind with the cell binding metal oxide; irradiating the solid support with a laser to disrupt the cells bound to the cell binding metal oxide to release a nucleic acid that binds with the cell binding metal oxide; introducing a washing buffer to the solid support to remove the cell-containing sample solution that is not bound to the cell binding metal oxide; and introducing a nucleic acid eluting buffer to the solid support to elute the nucleic acid bound to the cell binding metal oxide.

Thus, according to one embodiment of the invention, cell concentration, cell lysis and nucleic acid purification can be accomplished in a single chip. This is an improvement over conventional methods, which require multiple steps for cell concentration and nucleic acid purification. Furthermore, separate chips or chambers are needed for each step of the conventional methods, further requiring multiple valves and pumps. Therefore, conventional processes cannot be performed in a single chip.

FIG. 1 illustrates a method of concentrating cells, disrupting cells, and purifying nucleic acids released by the cells in a single chip or chamber, according to an embodiment of the invention. Referring to FIG. 1, cells are concentrated on a solid support having a pillar structure which is surface treated with a metal oxide having a hydrophobic property, I.e., a cell binding metal oxide. Subsequently, the solid support is irradiated with a laser, lysing the concentrated cells. The cell lysis enhancing metal oxide layer on the pillar structure enhances absorption of light at the wavelength of the laser, thereby enhancing efficiency of cell lysis. The nucleic acid released from the lysed cells also binds with the cell binding metal oxide and can be purified from the cell lysate using a washing buffer and an eluting buffer. According to one embodiment, all of the processes described above are performed in a single chip or chamber.

According to an embodiment of the invention, a metal oxide is deposited on a solid support, a cell-containing sample solution is added thereto, and then the cells bind to the solid support. Then, the cells bound to the solid support are irradiated with a laser beam, disrupting or lysing the cells, and nucleic acids released from the lysed cells are bound to the solid support. Once the nucleic acid from the lysed cells have bound to the solid support, a washing buffer is introduced to the solid support, thereby washing away any impurities in the cell lysate, such as cell debris and protein that are not bound to the solid support. Once the impurities have been removed by washing, the nucleic acid bound to the solid support can be eluted from the solid support by adding a nucleic acid eluting buffer. Finally, the eluted nucleic acid can be used in subsequent processes, as described below.

In one embodiment of the invention, metal oxide deposition on the solid support is performed by first depositing a cell lysis enhancing metal oxide layer on the solid support, and then depositing a cell binding metal oxide layer thereon.

The cell lysis enhancing metal oxide is a material that can enhance cell lysis upon irradiation with a laser beam, for example by enhancing absorption of light at the wavelength of the laser. The cell lysis enhancing metal oxide performs a similar function to that of a magnetic bead performing cell lysis. In one embodiment, the metal oxide is $Fe_2O_3$.

A cell binding metal oxide has the ability to bind cells. In an embodiment, the cell binding metal oxide has a hydrophobic property to enable cell binding. In some embodiments, the cell binding metal oxide also has the ability to bind nucleic acids. In one embodiment, the cell binding metal oxide is $Al_2O_3$. Generally, the layer of cell binding metal oxide should be transparent such that a laser beam can pass through the layer of cell binding metal oxide and then reach the layer of cell lysis enhancing metal oxide.

Figure 2:
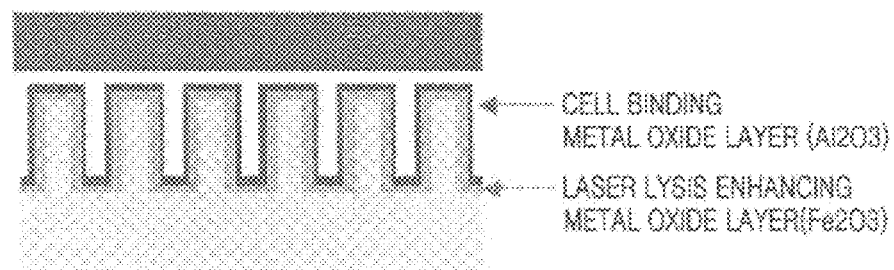
FIG. 2 is a diagram illustrating a chip having a pillar structure, that is a solid support on which a cell lysis metal oxide and a cell binding metal oxide are deposited according to the present invention.

FIG. 2 is a diagram illustrating a solid support on which a metal oxide is deposited according to an embodiment of the invention, that is, a cell lysis enhancing metal oxide is deposited on the solid support, and then a cell binding metal oxide is deposited on the solid support. As demonstrated by FIG. 2, the solid support can be a chip having a pillar structure. The chip can also have a planar structure. In FIG. 2, $Fe_2O_3$ is used as the cell lysis enhancing metal oxide, and $Al_2O_3$ is used as the cell binding metal oxide. $Fe_2O_3$ absorbs light having a wavelength of 808 nm, thereby enhancing cell lysis by laser irradiation at that wavelength.

In one embodiment of the invention, the cell binding metal oxide, or the cell lysis enhancing metal oxide can be, for example, $Al_2O_3$, $TiO_2$, $Ta_2O_3$, $Fe_2O_3$, $Fe_3O_4$, or $HfO_2$. In an exemplary embodiment, the cell binding metal oxide is $Al_2O_3$ and the cell lysis enhancing metal oxide is $Fe_2O_3$.

In another embodiment of the invention, the solid support can be, for example, slide glass, a silicon wafer, a magnetic bead, polystyrene, a membrane, a metal plate, or the like. The solid support can be any water-insoluble support material on which a metal oxide can be deposited. When a solid support is soluble in water, it can be difficult to purify and separate a nucleic acid solution from the solid support. In addition, use of a solid support having a large surface area is desirable for maximizing cell binding because more metal oxide can be deposited thereon. Therefore, for the case of a solid support material having a planar structure, such as slide glass or a wafer, the surface of the planar solid support material can be processed to create a pillar structure to increase its surface area.

In one embodiment of the invention, the cell-containing sample solution can have a pH in the range of 3-10. When the pH of the cell-containing solution falls outside of this range, the binding efficiency of the cells or the nucleic acids to the solid support on which the cell binding metal oxide is deposited decreases. In addition, when the pH of the cell-containing solution falls outside of this range the nucleic acid can be physically and chemically denatured affecting subsequent processes or analysis of the nucleic acid.

In one embodiment of the invention, the washing buffer can have a pH in the range of 3-10. When the pH of the washing buffer falls outside this range, the binding efficiency of the nucleic acid to the solid support on which the cell binding metal oxide is deposited decreases. In addition, when the pH of the washing buffer falls outside of this range the nucleic acid can be physically and chemically denatured, affecting subsequent processes or analysis of the nucleic acid.

In another embodiment of the invention, the buffer of the cell-containing sample solution, the washing buffer, and the nucleic eluting buffer can be, for example, a phosphate buffer, an acetate buffer, a citrate buffer, a Tris buffer, a sulfate buffer, and the like.

In one embodiment, the cell-containing solution, can comprise, for example, a phosphate buffer, an acetate buffer, a citrate buffer, a Tris buffer, a sulfate buffer, or the like. The buffer of the cell-containing solution can comprise a concentration in the range of about 10 to about 1,000 mM. When the concentration of the buffer of the cell-containing solution is less than about 10 mM, the binding efficiency of the cells to the solid support on which the cell binding metal oxide is deposited decreases. When the concentration of the buffer of the cell-containing solution is greater than about 1,000 mM, it is difficult to prepare a solution.

In one embodiment, the washing buffer, can be, for example, a phosphate buffer, an acetate buffer, a citrate buffer, a Tris buffer, a sulfate buffer, and the like. The concentration of the washing buffer can be about 10 to about, 1,000 mM. When the concentration of the washing buffer is less than about 10 mM, the washing efficiency of impurities such as cell debris or protein decreases. When the concentration of the washing buffer is greater than about 1,000 mM, it is difficult to prepare a solution.

In one embodiment, the nucleic acid eluting buffer, can be, for example, a phosphate buffer, an acetate buffer, a citrate buffer, a Tris buffer, a sulfate buffer, and the like. The nucleic acid eluting buffer may have a pH in the range of 8-10. When the pH of the nucleic acid eluting buffer is less than pH 8, the eluting efficiency of the nucleic acid from the cell binding metal oxide layer on the solid support decreases. When the pH of the nucleic acid eluting buffer is greater than pH 10, subsequent processes can be affected.

In an embodiment of the invention, the concentration of the nucleic acid eluting buffer may be about 10 to about 100 mM. When the concentration of the nucleic acid eluting buffer falls outside of this range, the efficiency of eluting the bound nucleic acid from the solid support on which a cell binding metal oxide is deposited decreases, as well as affecting subsequent processes such as nucleic acid analysis.

In one embodiment of the invention, the metal oxide can be deposited on a solid support using any known technique, such as physical vapor deposition (PVD), atomic layer deposition (ALD), a sol-gel method, or the like.

PVD is a method that is used in thin film formation. Since a thin film can be obtained relatively simply by low temperature treatment that cannot be performed using other methods, PVD has been favored as a means of surface curing. Examples of PVD methods include an evaporation deposition method that does not use ions, a sputtering method that uses ions, an ion plating method, an ion implantation method, an ion beam mixing method, and the like. Since a good film can be formed at a low temperature efficiently using ion energy, use of the ion plating method, the ion implantation method, the ion beam mixing method, etc. are favored, Metal is evaporated when heated in a vacuum, and this principle is applied in the evaporation deposition method. This method is performed under high vacuum conditions of less than $10^{-5}$ Torr and uses metal, or one of a variety of compounds, as a coating material. The method has been applied in making optical elements such as a lens, a mirror, or the like; all kinds of electric elements; and plastic elements, but it is rarely used for surface curing. When a particle having high energy is collided with a target material, atoms or molecules are ejected from the target material, and this phenomenon is called sputtering. In sputtering, a target material and a substrate form an anode and a cathode, respectively, and then a high pressure of about $10^{-2}$ Torr is applied between the anode and cathode under Ar atmosphere, and as a result, Ar gas around the anode is ionized to be $Ar^+$ and then the $Ar^+$ is collided with the anode. Molecules or atoms ejected by the ion bombardment are bound to the substrate, that is, the cathode, to form a thin film. Examples of sputtering include DC sputtering, RF sputtering, bias sputtering, magnetron sputtering and the like, and in particular, magnetron sputtering is a high speed sputtering method and favored in various fields. Through the PVD ion plating method, a hard film that has the best adhesion and a thickness of more than microns (μm) can be obtained. Thus, the method can be also applied to fields such as tools or molds, etc.

In an ALD method, a molecule is absorbed into a wafer surface using a chemically sticking property and then substituted. Since absorption and substitution are alternatively performed, ultrafine layer-by ultrafine layer deposition is possible, and an oxide and a thin metal film can be stacked as thin as possible. Also, since a suitable film can be formed at a lower temperature (less than 500° C.) than can be formed using a chemical vapor deposition (CVD) method, the ALD method is suitable for System-on-Chip (SoC) manufacture.

In a sol-gel method, a metal oxide having a colloid form is prepared through a hydrolysis reaction of a metal halide or alkoxide. The sol-gel method is a representative method of preparing a coating solution of titanium dioxide (TiO2). Physical characteristics of the titanium dioxide prepared, such as a particle size, crystalline properties, and the like, are affected by the kinds of alkoxide used, the reaction conditions (e.g., temperature, pH, molar ratio between reactants, etc.), and the like.

In another embodiment of the invention, the process in which a cell is bound to the solid support and the nucleic acid eluting process can be performed under either static or fluidic conditions. That is, a cell or a virus can be brought into contact with a solid support by flowing a cell-containing sample solution through a fluidic control system. In the fluidic control system, a solid support can have a plane form, but can also have a pillar structure providing additional surface area to bind more cells by increasing the opportunity for contact between the solid support and the cells.

In another embodiment, a method in which a nucleic acid is eluted from the solid support and then the eluted nucleic acid is detected can be additionally included. According to this embodiment, the eluted nucleic acid can be detected using an electrophoretic method, a nucleotide sequencing method, a restriction enzyme analysis, or the like.

In one embodiment of the invention, a method in which nucleic acid is eluted from the solid support and then the eluted nucleic acid, or a portion of the nucleic acid, is amplified can be additionally included. According to this embodiment, when the amount of eluted nucleic acid is below the limits of direct detection methods, the eluted nucleic acid can be amplified using a PCR method, such that the nucleic acid can be easily detected.

In one embodiment of the invention, the nucleic acid amplification process can be performed without removing the nucleic acid eluting buffer. Generally, the nucleic acid eluting buffer has a very similar composition to the buffer used for the nucleic acid amplification. In view of the similarities between the nucleic acid eluting buffer and the nucleic acid amplification buffer, the nucleic acid eluted in the eluting buffer can be amplified immediately without the need to remove the eluting buffer.

In another embodiment of the invention, the laser can be a pulse laser or a continuous wave laser. The pulse laser should have an output of more than 1 mJ/pulse, and the continuous wave laser should have an output of more than 10 mW. Preferably, the output of the pulse laser is more than 3 mJ/pulse, and the output of the continuous wave laser is more than 100 mW. When the output of the pulse laser is less than 1 mJ/pulse and the output of the continuous wave laser is less than 10 mW, the lasers cannot transmit enough energy to disrupt cells, resulting in incomplete lysis.

In another embodiment, the laser can be generated in a wavelength range of more than 400 nm, and preferably in the range of about 750 nm to about 1,300 nm. When the laser has a wavelength range of less than 400 nm, the DNA can become denatured or damaged. Furthermore, the laser can be generated at two or more different wavelengths, provided that the laser produces at least one wavelength within the wavelength range described above.

According to another embodiment of the invention, there is provided a chip. The chip comprises a solid support comprising a cell lysis enhancing metal oxide layer and a cell binding metal oxide layer. In one embodiment the cell lysis enhancing metal oxide and then the cell binding metal oxide are sequentially deposited on the solid support.

According to the current embodiment of the invention, the chip is arranged to perform a process of cell lysis and nucleic acid purification in the chip. In the chip, the cell lysis enhancing metal oxide layer enhances cell lysis by irradiation with a laser beam. The solid support can be any material on which a metal oxide can be deposited, but should be insoluble in water. When the solid support is soluble in water, it is difficult to separate the solid support from a nucleic acid solution. The solid support can be, for example, a slide glass, a silicon wafer, a magnetic bead, polystyrene, a membrane, a metal plate, or the like. The solid support can have a plane or pillar structure. However, the solid support advantageously has a large surface area to maximize cell binding. Therefore, for the case of a planar support material, such as glass or a wafer, the surface can be processed to have a pillar structure in order to increase surface area.

For the chip according to the current embodiment of the invention, the cell binding metal oxide or cell lysis enhancing metal oxide can be, for example, $Al_2O_3$, $TiO_2$, $Ta_2O_3$, $Fe_2O_3$, $Fe_3O_4$, or $HfO_2$. Preferably, the cell binding metal oxide is $Al_2O_3$, and the cell lysis enhancing metal oxide is $Fe_2O_3$.

According to another embodiment, the invention is directed to an apparatus for disrupting cells and purifying nucleic acids. The apparatus comprises the chip described above; and a laser source for generating a laser. In the apparatus, disrupting cells and purifying nucleic acids is performed in a single chip.

In one embodiment of the apparatus, the laser can be a pulse laser or a continuous wave laser. The pulse laser should have an output of more than 1 mJ/pulse, and the continuous wave laser should have an output of more than 10 mW. Preferably, the output of the pulse laser is more than 3 mJ/pulse, and the output of the continuous wave laser is more than 100 mW. When the output of the pulse laser is less than 1 mJ/pulse and the output of the continuous wave laser is less than 10 mW, the lasers cannot transmit enough energy to disrupt cells, which may be a problem.

In an embodiment of the apparatus, the laser may be generated in a wavelength range of more than 400 nm, and preferably in the range of about 750 nm to about 1,300 nm. When the laser is in a wavelength range of less than 400 nm, the nucleic acid can be denatured or damaged. Furthermore, the laser can have more than two different wavelengths, provided that the laser has at least one wavelength within the wavelength range described above.

The present invention will now be described in further detail with reference to the following examples. These examples are for illustrative purposes only and are not intended to limit the scope of the present invention.

EXAMPLES

Example 1

Manufacture of Chip on which Metal Oxide is Deposited

For this example, a chip on which metal oxide was deposited was manufactured by plasma assisted deposition ("PAD"), which is a PVD method, and by ALD. First, pillars were formed by photolithography and dry etching. A 4-inch silicon wafer was coated with positive photoresist, (Model: AZ1512) using a spin coating method at 4000 RPM for 40 seconds, and then baked at 95° C. for 1.5 minutes. In an aligner (Model: EV620), the positive photoresist-coated wafer was irradiated with an I-line UV light (wavelength: 365 nm) for 4.5 seconds. Then the positive photoresist that was exposed to the UV light was removed using a developer (Model: AZ MIF 300) to form a pillar pattern. The obtained wafer having the pillar pattern was dry etched to a depth of 100 μm using a dry etching apparatus (Model: ICP-STS) to finally form rectangular parallelepiped pillars each having a size of 25 μm×25 μm×100 μm (width×length×height). $Fe_2O_3$ metal oxide used as a cell lysis enhancing layer was deposited to a depth of 300 nm on the rectangular parallelepiped pillar surfaces using a plasma assisted deposition method (PAD, model: APS1104). Subsequently, a glass plate having pores of 1 mm diameter was coupled to the chip having the pillars using an anodic binding apparatus (Model: TPS-1000) at 370° C. while 700 V was applied. Then, a metal oxide, $Al_2O_3$, used as a cell binding and nucleic acid binding layer was deposited on the chip surface through the pores of the glass plate to a depth of 10 nm at 400° C. using an ALD apparatus (atomic layer deposition, Model: MOOHAN) to complete the chip.

Figure 3A:
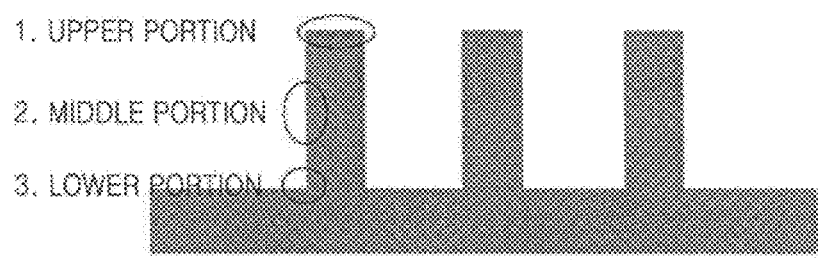
FIG. 3A is a diagram illustrating an upper portion, a middle portion and a lower portion of the solid support of a chip on which metal oxide used as a cell lysis enhancing layer was deposited.
Figure 3B:
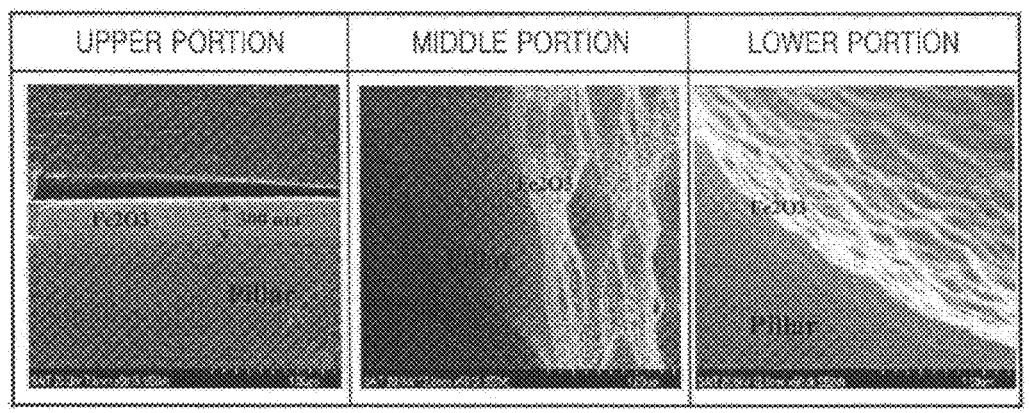
FIG. 3B provides a series of field emission-scanning electron microscope (FE-SEM) images of an upper portion, a middle portion and a lower portion of the solid support of the chip of FIG. 3A.

FIG. 3A schematically represents an upper portion, a middle portion and a lower portion of a chip on which a metal oxide used as a cell lysis enhancing layer ($Fe_2O_3$) was deposited. FIG. 3B is a series of field emission-scanning electron microscope ("FE-SEM") images of the chip taken in each position described above. As can be seen in FIG. 3B, a $Fe_2O_3$ deposition film having a depth of 300 nm is formed on the upper portion of the pillar, while on the middle and lower portions of the pillar the $Fe_2O_3$ layer has a thickness of 200 and 250 nm, respectively. Therefore, the cell lysis enhancing metal oxide is considered to be deposited satisfactorily.

Example 2

Cell Binding Using the Chip

For this example, a cell was bound to a chip according to an embodiment of the invention in a fluidic control system. First, a mixture of saliva filtered using a filter paper (pore size 6 μm, Whatman) and *E. coli* BL21 (Stratagene Cat. No. 200133) cell was used as a cell-containing sample. The cell-containing sample (cell concentration: $OD_{600}$=0.001) and a binding buffer (100 mM phosphate buffer, pH 4) were mixed in a ratio of 1:1. A volume of 680 μL of the mixture was injected to the chip at a flow rate of 400 μL/min using a syringe pump (HARVARD, PHD2000) The *E. coli* cells then bound to the chip.

Figure 4:
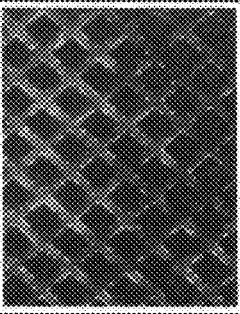
FIG. 4 provides a FE-SEM image, as well as data illustrating the binding efficiency of E. coli cells with different kinds of chips.

FIG. 4 provides a series of FE-SEM images demonstrating the binding efficiency of *E. coli* cells to different kinds of chips. In FIG. 4, the $Fe_2O_3/Al_2O_3$ chip uses $Fe_2O_3$ as the cell lysis enhancing metal oxide and $Al_2O_3$ as the cell binding metal oxide. In FIG. 4, an $Al_2O_3$ chip uses only $Al_2O_3$ as a metal oxide. Also, the control in FIG. 4 shows the results for a cell free sample in which the binding buffer without *E. coli* cells was passed through a $Fe_2O_3/Al_2O_3$ chip. A plating method was used for determination of the binding efficiency of *E. coli* to the chip, that is, binding efficiency was measured by plating a sample of the solution in a petri dish wherein *E. coli* growth medium is included. A sample of the solution was taken for plating before and after the solution was passed through the chip. Whether a cell was bound to the chip was determined using a LIVE/DEAD® BACLIGHT™ Bacterial viability kit (Molecular Probes). For the LIVE/DEAD® BACLIGHT™ Bacterial viability kit, living cells are dyed green by Cyto®9 nucleic acid stain dye and dead cells are dyed red by Propidium Iodide ("PI") dye.

In FIG. 4, using the Cyto9/PI staining, produced a green image, showing that living *E. coli* cells were bound to the $Fe_2O_3/Al_2O_3$ chip and the $Al_2O_3$ chip. The control chip did not show a green image due to the absence of any cells in the binding buffer. As indicated in FIG. 4, the binding efficiency of *E. coli* to the $Fe_2O_3/Al_2O_3$ chip and to the $Al_2O_3$ chip was about 80%, so that *E. coli* is considered to be efficiently bound to both chips.

Example 3

Cell Lysis Using the Chip

In this example, cell lysis was performed by irradiating the cells bound to the chips of Example 2 with a laser beam.

Figure 5:
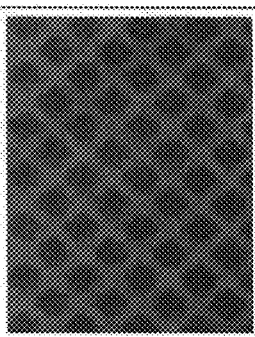
FIG. 5 is a FE-SEM image showing E. coli cell lysis using different kinds of chips.

The cells were lysed by irradiating the $Fe_2O_3/Al_2O_3$ chip, the $Al_2O_3$ chip and the control chip for 40 seconds with a 2 W laser beam. After cell lysis, staining was performed using the LIVE/DEAD® BACLIGHT™ Bacterial viability kit as described above. FIG. 5 is a FE-SEM image showing the results of the *E. coli* cell lysis efficiency with regard to the three different kinds of chips. In FIG. 5, the $Fe_2O_3/Al_2O_3$ chip showed a higher intensity of red color than did the $Al_2O_3$ chip, indicating an increased number of dead cells on the $Fe_2O_3/Al_2O_3$ chip. The control chip did not show a red image due to the absences of any bound cells. Accordingly, it can be seen that cells bound to the $Fe_2O_3/Al_2O_3$ chip according to an embodiment of the invention was efficiently lysed. This example also demonstrates that cell lysis was more efficient when a cell lysis enhancing metal oxide ($Fe_2O_3$ in the present example) is used on the chip in addition to the cell-binding metal oxide ($Al_2O_3$).

Example 4

Nucleic Acid Purification Using the Chip

In this example, the nucleic acid released from the lysed cells in Example 3 was purified. To remove impurities from the *E. coli* genomic DNA in the cell lysates produced in Example 3, a washing buffer (10 mM phosphate buffer, pH 4) was injected to the chip at a flow rate of 100 μL/min using a syringe pump (HARVARD, PHD2000). Subsequently, to elute the washed nucleic acid, a nucleic acid eluting buffer (50 mM $Na_2SO_4$, pH 10) was injected to the chip at a flow rate of 1000 μL/min using a syringe pump (HARVARD, PHD2000).

Figure 6:
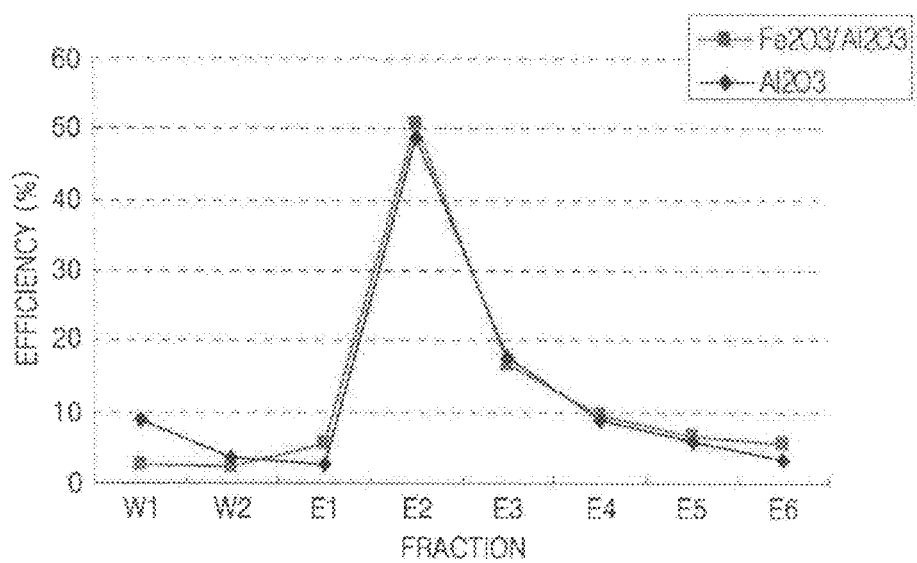
FIG. 6 is a graph showing the eluting efficiency of E. coli genomic DNA (gDNA) with respect to washing buffers and nucleic acid eluting buffers.

FIG. 6 is a graph showing the elution efficiency of *E. coli* genomic DNA (gDNA) from the chip following introduction of the washing buffer and then the nucleic acid eluting buffer to the chip. In FIG. 6, W1 and W2 each refer to a 25 μl fraction of the washing buffer, and E1 through E6 each refer to a 25 μl fraction of the nucleic acid eluting buffer. Further, the elution efficiency refers to the amount of *E. coli* genomic DNA eluted in each fraction with respect to the total amount of *E. coli* genomic DNA eluted. As can be seen in FIG. 6, only minute amounts of *E. coli* genomic DNA eluted in the washing buffer regardless of whether the $Fe_2O_3/Al_2O_3$ chip or the $Al_2O_3$ chip was used. FIG. 6 further demonstrates that most of the *E. coli* genomic DNA eluted in the nucleic acid eluting buffer. Therefore, it can be seen that a nucleic acid can be efficiently purified from the chip after cells are lysed using a single chip when the method of the invention is used.

Example 5

Cell Enrichment Using the Chip

For this example, the effect of cell enrichment using a chip according to an embodiment of the invention was determined. In particular, the amount of E. coli genomic DNA purified according to the method of Example 4, was quantified as a function of the amount of E. coli input to the chip. A method of measuring cell enrichment was performed by lysing samples of E. coli cells by laser irradiation in an Eppendorf tube as a function of cell concentration and then quantifying the amount of DNA from the lysed cells using PICOGREEN®. Based on this, a quantification curve of the amount of DNA after lysis as a function of initial cell concentration was drawn. Then, the amount of DNA eluted from the chip according to an embodiment of the invention could be converted to a cell concentration to calculate enrichment efficiency.

Figure 7:
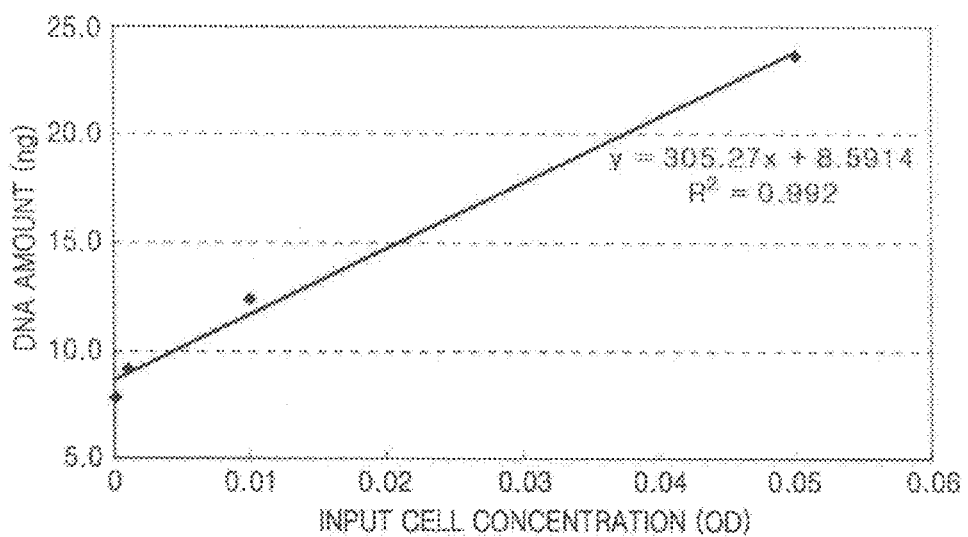
FIG. 7 is a graph illustrating a quantification curve of DNA as a function of concentration of input E. coli cells.

FIG. 7 is a graph illustrating a quantification curve of DNA as a function of the input E. coli cell concentration. As can be seen in FIG. 7, the input E. coli cell concentration was nearly proportional to the amount of the E. coli genomic DNA. The amount of E. coli genomic DNA purified using the chip according to an embodiment of the invention could be converted to a cell concentration using the quantification curve of FIG. 7. The results are shown in Table 1 below.

TABLE 1

| | $Fe_2O_3/Al_2O_3$ chip | $Al_2O_3$ chip |
|---|---|---|
| Input cell concentration ($OD_{600}$) | 0.001 | 0.001 |
| Output cell concentration ($OD_{600}$) | 0.014 | 0.016 |
| Enrichment ratio | 14 times | 16 times |

As can be seen in Table 1, E. coli cell is enriched up to 14 times through 16 times when the chip according to an embodiment of the invention is used. Therefore, when detecting nucleic acids from a test sample having a very low cell concentration, the method according to an embodiment of the invention can be effectively used.

Example 6

PCR Amplification of Nucleic Acid Purified Using the Chip

For this example, PCR was performed using the nucleic acid purified using the chip according to an embodiment of the invention. PCR was performed under a standard condition known to those of ordinary skill in the art. E. coli genomic DNA was purified according to the method disclosed in Example 4. The amount of a PCR amplification product of the purified E. coli genomic DNA was determined. A method of measuring cell enrichment was performed by lysing samples of E. coli cells by laser irradiation in an Eppendorf tube as a function of E. coli cell concentration, and then amplifying the E. coli genomic DNA by PCR and quantifying the PCR product by LABCHIP®. Based on these experiments, a quantification curve of amount of PCR product after lysis as a function of initial cell concentration was drawn, and then the amount of the PCR product obtained with the eluted E. coli genomic DNA was converted to cell concentration to calculate enrichment efficiency.

Figure 8:
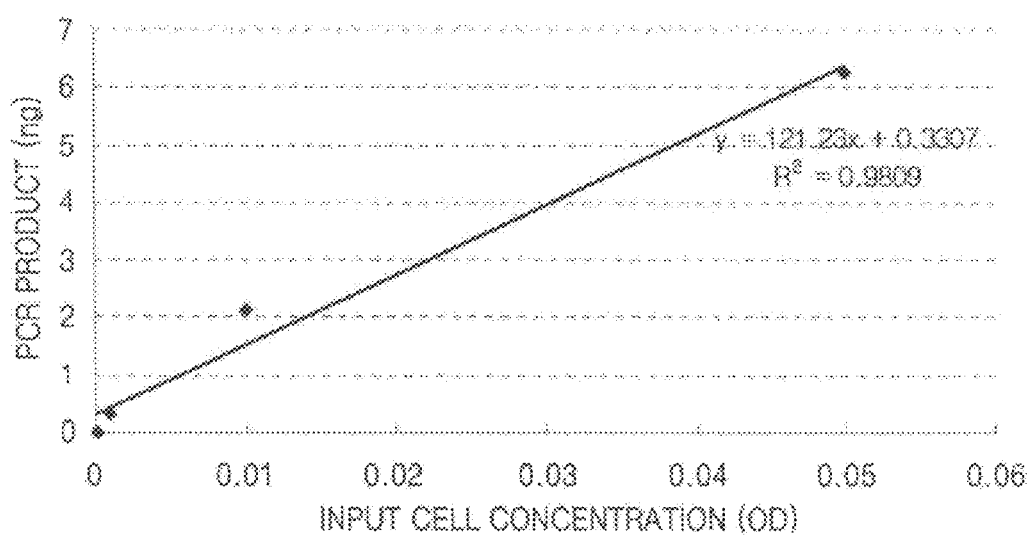
FIG. 8 is a graph showing a quantification curve of an amplified PCR product as a function of concentration of input E. coli cells.

FIG. 8 is a graph illustrating a quantification curve of the amplified PCR product with respect to cell concentration of input E. coli. As can be seen in FIG. 8, the cell concentration of input E. coli is nearly proportional to the amount of the PCR product. A PCR product obtained using E. coli genomic DNA purified using a chip according to an embodiment of the invention was then converted to a cell concentration using the quantification curve of FIG. 8, and the results are shown in Table 2 below.

TABLE 2

| | $Fe_2O_3/Al_2O_3$ chip | $Al_2O_3$ chip |
|---|---|---|
| Input cell concentration ($OD_{600}$) | 0.001 | 0.001 |
| PCR product amount (ng) | 0.88 | 0.65 |
| Output cell concentration ($OD_{600}$) | 0.005 | 0.003 |
| Enrichment ratio | 5 times | 3 times |

As can be seen in Table 2, E. coli cells are concentrated up to 3 times through 5 times using the chip according to the invention. The results described in Table 2 differ slightly from the results provided in Table 1. The difference can be accounted for by taking into account the different methods of DNA quantification used.

In summary, by developing a single chip wherein it is possible to perform cell enrichment, cell lysis, and nucleic acid purification, integration of these processes on a Lab-On-a-Chip can be achieved. Accordingly, the three processes can be performed in one chip, reducing the cost of manufacturing the chip.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of disrupting cells on a chip, the method comprising:
   depositing a cell lysis enhancing metal oxide layer on a chip having pillar structures on a surface of a solid support and wherein the cell lysis enhancing metal oxide layer is deposited on a surface of the pillar structures;
   depositing a cell binding metal oxide layer on the cell lysis enhancing metal oxide layer;
   binding cells present in a cell-containing sample solution to the cell binding metal oxide layer;
   irradiating a chip with cells bound thereon with a laser beam to disrupt the cells,
   wherein the cell lysis enhancing metal oxide is $Fe_2O_3$ and the cell binding metal oxide is $Al_2O_3$.

2. A method of disrupting cells and purifying nucleic acids using a single chip, the method comprising:
   introducing a cell-containing sample solution to a solid support having pillar structures on a surface,
   wherein the solid support comprises a cell lysis enhancing metal oxide layer deposited on a surface of the pillar structures and a cell binding metal oxide layer deposited on the cell lysis enhancing metal oxide layer,
   wherein the cell lysis enhancing metal oxide is $Fe_2O_3$ and the cell binding metal oxide is $Al_2O_3$,
   wherein the cells bind with the cell binding metal oxide;
   irradiating the solid support with a laser to disrupt the cells bound to the cell binding metal oxide to release a nucleic acid that binds with the cell binding metal oxide;
   binding the released nucleic acid to the cell binding metal oxide layer;
   introducing a washing buffer to the solid support to remove the cell-containing sample solution that is not bound to the cell binding metal oxide; and
   introducing a nucleic acid eluting buffer to the solid support to elute the nucleic acid bound to the cell binding metal oxide.

3. The method of claim 2, wherein the solid support is selected from the group consisting of glass, a silicon wafer, a magnetic bead, polystyrene, and a metal plate.

4. The method of claim 2, wherein the cell-containing sample solution and the washing buffer have a pH of 3-10.

5. The method of claim 2, wherein the cell-containing sample solution comprises a buffer selected from the group consisting of phosphate, acetate, citrate and Tris buffers, and
   wherein the washing buffer and the nucleic acid eluting buffer are selected from the group consisting of phosphate, acetate, citrate and Tris buffers.

6. The method of claim 2, wherein the cell-containing sample solution comprises a buffer having a concentration of about 10 to about 1,000 mM and the washing buffer has a concentration of about 10 to about 1,000 mM.

7. The method of claim 2, wherein the nucleic acid eluting buffer has a pH of 8-10.

8. The method of claim 2, wherein the nucleic acid eluting buffer has a concentration of about 10 to about 100 mM.

9. The method of claim 2, further comprising
   detecting or amplifying the eluted nucleic acid.

10. The method of claim 9, wherein amplifying the eluted nucleic acid is performed without removing the nucleic acid eluting buffer.

11. The method of claim 2, wherein the laser is a pulse laser or a continuous wave laser.

12. The method of claim 11, wherein the pulse laser has an output of more than 1 mJ/pulse, and the continuous wave laser has an output of more than 10 mW.

* * * * *